United States Patent
Ueda et al.

(10) Patent No.: US 12,329,438 B2
(45) Date of Patent: Jun. 17, 2025

(54) DENTAL TREATMENT APPARATUS

(71) Applicant: J. MORITA MFG. CORP., Kyoto (JP)

(72) Inventors: Tomoaki Ueda, Kyoto (JP); Kyohei Kato, Kyoto (JP); Kazunari Matoba, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 37 days.

(21) Appl. No.: 17/535,251

(22) Filed: Nov. 24, 2021

(65) Prior Publication Data

US 2022/0160417 A1   May 26, 2022

(30) Foreign Application Priority Data

Nov. 26, 2020   (JP) ................................ 2020-195973

(51) Int. Cl.
*A61B 18/14* (2006.01)
*A61B 18/12* (2006.01)
*A61C 5/42* (2017.01)

(52) U.S. Cl.
CPC .......... *A61B 18/14* (2013.01); *A61B 18/1206* (2013.01); *A61C 5/42* (2017.02); *A61B 2018/128* (2013.01)

(58) Field of Classification Search
CPC ........ A61C 5/42; A61B 18/14; A61B 18/1206
See application file for complete search history.

(56) References Cited

U.S. PATENT DOCUMENTS

| | | | | | |
|---|---|---|---|---|---|
| 4,784,142 | A | * | 11/1988 | Liss ....................... | A61N 1/326 607/148 |
| 5,312,396 | A | * | 5/1994 | Feld ....................... | B23K 26/06 606/7 |
| 6,482,008 | B2 | * | 11/2002 | Perdomini ........... | A61C 19/041 433/32 |
| 6,664,498 | B2 | * | 12/2003 | Forsman ............ | B23K 26/0676 219/121.85 |

(Continued)

FOREIGN PATENT DOCUMENTS

CN   1224339 A   7/1999
CN   201558164 U   8/2010

(Continued)

OTHER PUBLICATIONS

Extended European Search Report issued on Apr. 4, 2022, in European Patent Application No. 21209870.1, 8 pages.

(Continued)

*Primary Examiner* — Nicholas D Lucchesi
*Assistant Examiner* — Hao D Mai
(74) *Attorney, Agent, or Firm* — Oblon, McClelland, Maier & Neustadt, L.L.P.

(57) ABSTRACT

A dental treatment apparatus is a dental treatment apparatus that energizes a dental treatment site such as a root canal with a high-frequency current. Included are a holder that holds an electrode placed at the dental treatment site, a power supply that energizes the electrode with the high-frequency current, and control circuitry that causes, during the energization operation, the power supply to provide stop (Continued)

period where the energization of the electrode with the high-frequency current is stopped between single energization period and next single energization period.

14 Claims, 8 Drawing Sheets

(56) References Cited

U.S. PATENT DOCUMENTS

| | | | |
|---|---|---|---|
| 7,723,642 B2* | 5/2010 | Gu | H01L 21/485 219/121.61 |
| 7,838,794 B2* | 11/2010 | Gu | B23K 26/04 219/121.68 |
| 9,681,912 B2* | 6/2017 | Tsubuku | A61B 18/1445 |
| 2004/0267333 A1 | 12/2004 | Kronberg | |
| 2006/0257819 A1* | 11/2006 | Johnson | A61C 1/07 433/86 |
| 2010/0168742 A1* | 7/2010 | Shibata | A61B 18/148 606/42 |
| 2010/0209867 A1 | 8/2010 | Becker et al. | |
| 2011/0003226 A1 | 1/2011 | Markoski et al. | |
| 2011/0039226 A1 | 2/2011 | Armanino | |
| 2012/0322027 A1 | 12/2012 | Laxhuber | |
| 2016/0287317 A1* | 10/2016 | Tsubuku | A61B 18/1445 |
| 2017/0216579 A1 | 8/2017 | Becker et al. | |
| 2017/0265961 A1* | 9/2017 | Kato | A61C 3/02 |
| 2019/0269902 A1 | 9/2019 | Fregoso et al. | |
| 2021/0069756 A1* | 3/2021 | Lukac | A61N 5/0624 |
| 2021/0162202 A1 | 6/2021 | Fregoso et al. | |

FOREIGN PATENT DOCUMENTS

| | | |
|---|---|---|
| CN | 109925084 A | 6/2019 |
| EP | 2 345 388 A1 | 7/2011 |
| JP | 2000-515398 A | 11/2000 |
| JP | 4041165 B2 | 1/2008 |
| JP | 2011-193907 A | 10/2011 |
| JP | 2012-507385 A | 3/2012 |
| WO | WO97/46170 A1 | 12/1997 |
| WO | WO 2007/057878 A2 | 5/2007 |
| WO | WO 2008/053532 A1 | 5/2008 |
| WO | WO2008/114244 A1 | 9/2008 |
| WO | WO 2014/099064 A1 | 6/2014 |
| WO | WO 2015/122307 A1 | 8/2015 |

OTHER PUBLICATIONS

Bando, et al. "Application of electro-magnetic wave irradiation for endodontic treatment—EMAT (electro-magnetic apical treatment)", The Journal of Japan Endodontic Association, vol. 32, 2011, pp. 184-200 (with English Abstract).

Japanese Office Action issued on Jan. 31, 2023 in Japanese Patent Application No. 2020-195973 (with unedited computer-generated English translation), 6 pages.

Notification issued Jul. 11, 2023, in corresponding Japanese Patent Application No. 2020-195973 (with English Translation), 2 pages.

Information Offer Form issued Jun. 16, 2023, in corresponding Japanese Patent Application No. 2020-195973 (with English Translation), 6 pages.

Notice of Reasons for Refusal issued Jul. 25, 2023, in corresponding Japanese Patent Application No. 2020-195973 (with English Translation), 6 pages.

Yakuji Nipposha, Medical Device Center Foundation, "Basic Knowledge of Medical Devices 2nd Edition", Dec. 10, 2008, pp. 131-135.

Sakuragi, "Easy-tounderstand electric scalpel book—Know your weapon!", Kanehara Publishing Co., Ltd., Mar. 31, 2014, pp. 87-93.

Fukushima, "Knowing Bacteria: Changing the End", Eisue Shoten Publishing, Jun. 1, 1999, pp. 142-150.

Chinese Office Action issued Jan. 31, 2024, in Chinese Patent Application No. 202111394542.8, therein, 13 pages (with English Translation).

Chinese Office Action issued Jul. 24, 2024 in corresponding Chinese Application No. 2021113945428, filed Nov. 23, 2021 (with English translation), 8 pages.

* cited by examiner

DENTAL TREATMENT APPARATUS

CROSS-REFERENCE TO RELATED APPLICATIONS

This application claims priority under 35 U.S.C. § 119 from Japanese Patent Application No. 2020-195973, filed Nov. 26, 2020. The entire content of the above application is incorporated herein by reference.

BACKGROUND

Field

The present disclosure relates to a dental treatment apparatus that energizes a dental treatment site with a high-frequency current.

Description of the Background Art

In the dental field, root canal treatment for teeth may be performed to remove dental pulp or to mitigate inflammation at a root apex. In such a root canal treatment, a root canal is cut and widened with a reamer and a file, contaminated tissue or contaminants in the root canal are removed, and then the root canal is filled with a medicament.

The root canal, however, has a complex shape, and the shape differs from tooth type to tooth type and from person to person. It is therefore difficult for the root canal treatment to cut and widen some portion of the root canal even with a reamer and a file, which may cause an inflammation factor to remain such that the root canal cannot be widened and that inflammation occurs after the treatment.

Japanese Patent No. 4041165 discloses dental medical equipment that applies high-frequency electron pulses to the inside of a root canal. Such medical equipment applies, when a needle-shaped electrode (for example, a file) is inserted into a root canal, and a distal end of the needle reaches a root apex, the high-frequency electron pulses to cauterize dental pulp and the like.

Further, WO 2008/114244 A discloses a dental treatment apparatus that performs root canal treatment for reducing an inflammation factor, bacteria, and the like in the root canal of a tooth. In such a dental treatment apparatus, a dental instrument capable of communicating with a measuring instrument that measures the position of the root apex includes an electrode to be inserted into the root canal. The dental instrument is further capable of communicating with a unit that applies electric pulses. This allows the dental treatment apparatus to apply electric pulses to the root canal through the electrode inserted into the root canal to reduce an inflammation factor, bacteria, and the like in the root canal with the help of the application of electric pulses.

SUMMARY

Energization of the root canal with the high-frequency current using the dental treatment apparatus, however, may cause, when a position where the energization with the high-frequency current is performed, a current value with which the energization is performed, an energization period, or the like is not appropriate, a patient to complain of a pain caused by the energization with the high-frequency current. In particular, treatment without anesthesia tends to bring about such a situation. Although the energization of the root canal with the high-frequency current can be performed with the patient put under anesthesia to prevent the patient from complaining of a pain caused by the energization with the high-frequency current, it is required that the patient be anesthetized for each time the energization with the high-frequency current is performed. Therefore, in many cases, the energization of the root canal with the high-frequency current using the dental treatment apparatus is performed without anesthesia.

When the energization of the root canal with the high-frequency current using the dental treatment apparatus is performed without anesthesia, it is possible to perform treatment using a selected optimum current value so as to prevent the patient from complaining of a pain caused by the energization with the high-frequency current and prevent a high-frequency current larger than or equal to a current value at which nerves react from flowing through tissue where the nerves exist. The energization with the high-frequency current, however, is performed in order to cauterize infected tissue or contaminants, so that energization with a high-frequency current larger than or equal to the current value at which nerves react is normally performed, thereby causing the patient to frequently complain of a pain caused by the energization with the high-frequency current. Further, in some cases, a temperature excessively rises at a site energized with the high-frequency current by the dental treatment apparatus.

The present disclosure solves, at least, the above-described problems, and it is therefore an object of the present disclosure to provide a dental treatment apparatus capable of performing energization with a high-frequency current to the extent that a patient does not complain of a pain and preventing a temperature at an energized site from excessively rising.

A dental treatment apparatus according to the present disclosure energizes a dental treatment site with a high-frequency current. The dental treatment apparatus includes a holder, a power supply, and a controller. The holder holds an electrode placed at the dental treatment site. The power supply energizes the electrode with the high-frequency current. The controller causes, during energization operation, the power supply to provide a stop period where the energization of the electrode with the high-frequency current is stopped between a single energization period and the next single energization period.

The foregoing and other objects, features, aspects and advantages of the present disclosure will become more apparent from the following detailed description of the present disclosure when taken in conjunction with the accompanying drawings.

DETAILED DESCRIPTION

Hereinafter, embodiments according to the present disclosure will be described with reference to the drawings.

First Embodiment

Figure 1:
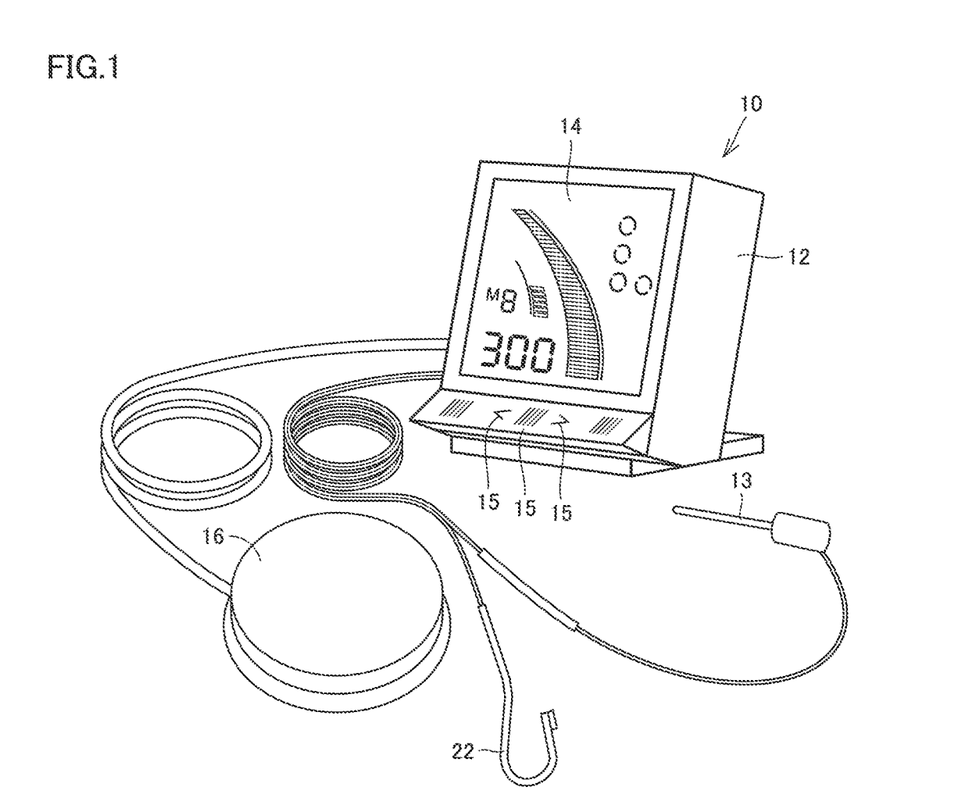
FIG. 1 is an external view of a dental treatment apparatus according to a first embodiment.
Figure 2:
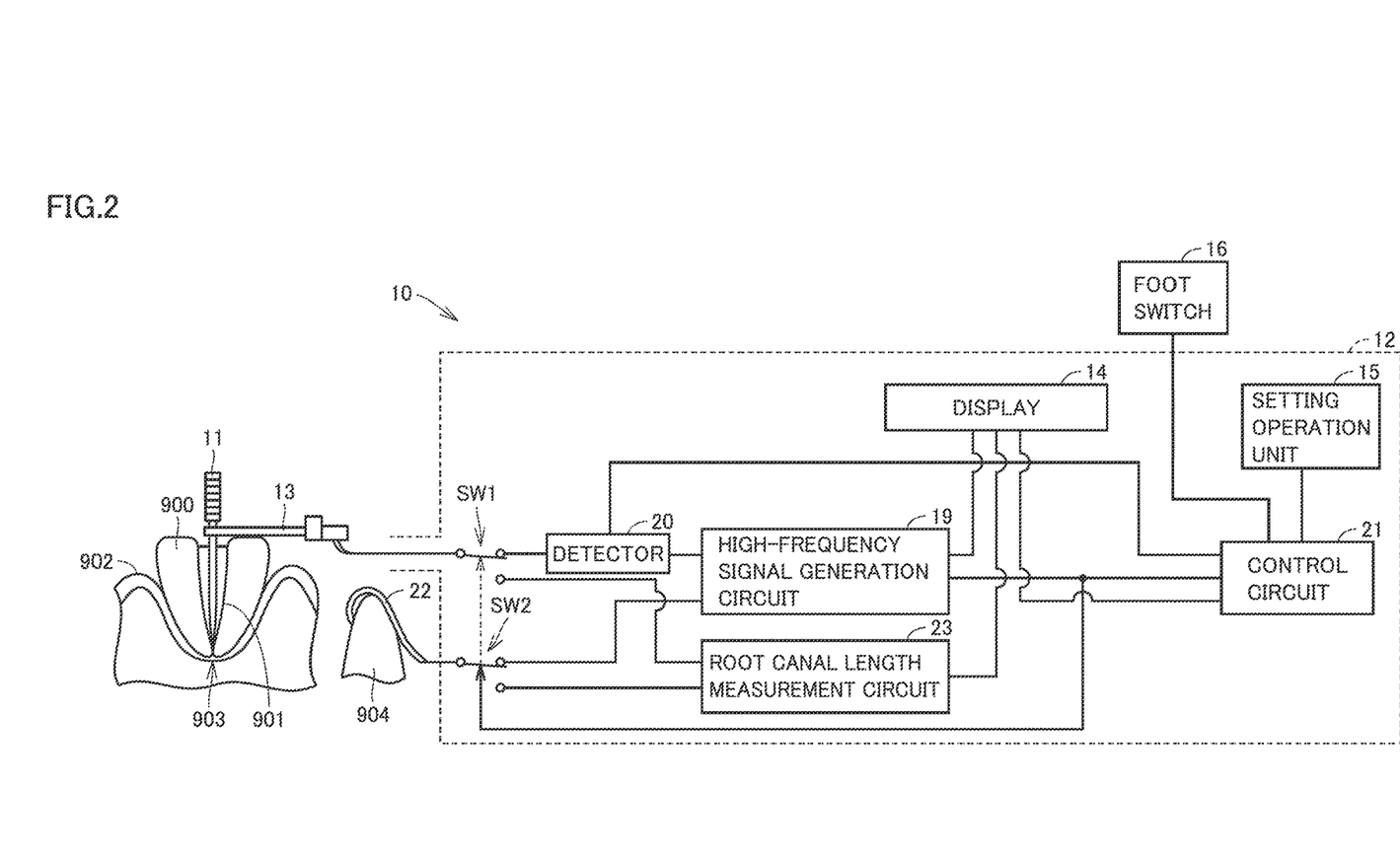
FIG. 2 is a block diagram of a configuration of the dental treatment apparatus according to the first embodiment.
Figure 3:
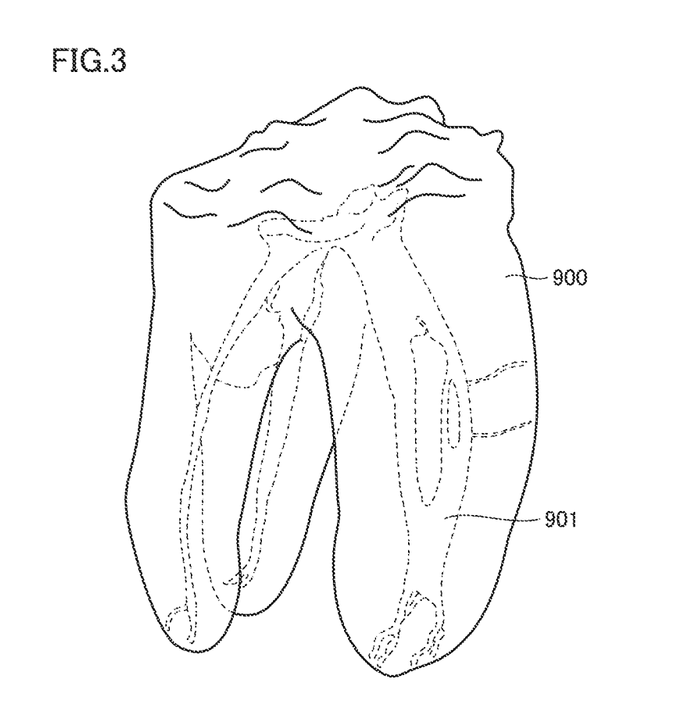
FIG. 3 is a diagram for schematically describing a root canal of a tooth.

FIG. 1 is an external view of a dental treatment apparatus according to a first embodiment. FIG. 2 is a block diagram of a configuration of the dental treatment apparatus according to the first embodiment. FIG. 3 is a diagram for schematically describing a root canal of a tooth. Root canal treatment of cutting and widening a root canal of a tooth is very difficult treatment because a degree to which a root canal is curved or a degree to which a root canal is calcified and blocked, and the like are different among individuals. A tooth 900 shown in FIG. 3 is a molar tooth, and each tooth includes a plurality of root canals 901. It is difficult to perform treatment on all such complex-shaped root canals. In particular, when there is a portion where it is difficult to cut and widen a root canal using cutting tools such as a reamer and a file, the root canal in the portion cannot be cut and widened, and dental pulp or an inflammation factor remains in the root canal, inflammation may occur after treatment.

Therefore, the dental treatment apparatus performs treatment in which an electrode is inserted into a root canal, and the electrode is energized with a high-frequency current. During this treatment, a human body, particularly a tooth, more particularly a root canal, a periodontal tissue, or a bone is energized with the high-frequency current, so that the energized portion, particularly a portion near the electrode and a portion having a high current density, is cauterized by Joule heat generated by the high-frequency current, reducing an inflammation factor, bacteria, and the like. Note that complete sterilization need not be achieved by this treatment, and it is sufficient that dental pulp or granulation can be thermally denatured to cause necrosis or deactivation. Further, this treatment is also referred to as electro-magnetic apical treatment (EMAT) and is disclosed in the literature (for example, Naoki Bando, Toshihiko Tominaga, Hiromichi Yumoto, Takashi Sumitomo, Saki Hirao, Koji Hirao, Takashi Matsuo, "Application of electro-magnetic wave irradiation for endodontic treatment-EMAT (electro-magnetic apical treatment)", 2011, The Journal of Japan Endodontic Association, vol. 32, pp. 184-200) and the like. This disclosure has reported that prognosis is extremely good because it is possible to reduce an inflammation factor, bacteria, and the like at the dental treatment site by energizing, with a high-frequency current, an affected part before and after treatment.

Energization of the root canal with the high-frequency current using the dental treatment apparatus, however, may cause, when a position where the energization with the high-frequency current is performed, a current value with which the energization is performed, an energization period, or the like is not appropriate, a patient to complain of a pain caused by the energization with the high-frequency current. Although the energization of the root canal with the high-frequency current can be performed with the patient put under anesthesia to prevent the patient from complaining of a pain caused by the energization with the high-frequency current, it is required that the patient be anesthetized for each time the energization with the high-frequency current is performed. Therefore, in many cases, the energization of the root canal with the high-frequency current using the dental treatment apparatus is performed without anesthesia.

When the dental treatment apparatus energizes the root canal with the high-frequency current without anesthesia, sufficient cauterization cannot be made on tissue because a current value of the high-frequency current at which the patient does not complain of a pain caused by the energization with the high-frequency current is extremely small. The energization with the high-frequency current is performed in order to cauterize infected tissue or contaminants, so that energization with a high-frequency current larger than or equal to the current value at which nerves react is normally performed, thereby causing the patient to frequently complain of a pain caused by the energization with the high-frequency current.

Therefore, in a dental treatment apparatus 10 according to the first embodiment, when the user continues energization operation of energizing a file 11 with the high-frequency current (for example, when stepping on a foot switch 16), a single energization period (for example, a period where energization is performed in response to single operation of foot switch 16) is not simply and continuously repeated, but a stop period where the energization of file 11 with the high-frequency current is stopped is provided between the single energization period and the next single energization period. This allows dental treatment apparatus 10 to perform energization with the high-frequency current to the extent that the patient does not complain of a pain and to prevent a temperature at an energized site from excessively rising, as compared with a configuration where the single energization period is simply and continuously repeated. Note that the stop period is a period where energization of file 11 with the high-frequency current is not performed and may include a period where foot switch 16 is not operated.

Hereinafter, a description will be given in detail of a configuration of dental treatment apparatus 10 according to the first embodiment. First, as shown in FIG. 1, dental treatment apparatus 10 includes an energizing unit 12 that energizes, with a high-frequency current, file 11 (see FIG. 2) that is a cutting tool, and a file holder 13 that holds file 11 and is capable of energizing, with the high-frequency current, file 11 attached to a distal end of file holder 13. Note that, in the present disclosure, file 11 attached to the distal end of file holder 13 and serving as an electrode to be placed at a dental treatment site will be described, but file holder 13 and file 11 may be integrated into a single unit.

File holder 13 is made of a substantially rod-shaped housing and is capable of holding a metal portion of file 11. File holder 13 can electrically connect the file and energizing unit 12 by holding the metal portion of file 11. Energizing unit 12 includes a display 14 and a setting operation unit 15 and is connected with a foot switch 16 and a passive electrode 22.

As shown in FIG. 2, energizing unit 12 includes a high-frequency signal generation circuit 19, a detector 20, a control circuit 21, a root canal length measurement circuit 23, and switches SW1, SW2 in addition to display 14 and setting operation unit 15.

Setting operation unit 15 includes setting buttons provided for setting how dental treatment apparatus 10 operates. Setting operation unit 15 allows a current value, frequency, energization period of the high-frequency current with which file 11 is energized, a display setting of display 14, and the like to be set. Herein, the energization period is a period where energization with the high-frequency current is performed in response to single energization operation and is also referred to as a single energization period. When the single energization period is divided into a plurality of continuous energization periods, the sum total of the plurality of continuous energization periods obtained as a result of the division corresponds to a cumulative energization period of the high-frequency current.

Foot switch 16 is an operation unit provided to control the energization with the high-frequency current, and a control signal is transmitted from control circuit 21 to high-frequency signal generation circuit 19 when a user steps on foot switch 16. High-frequency signal generation circuit 19 energizes file 11 with the high-frequency current set via setting operation unit 15 based on the control signal received. That is, the single energization period is repeated while the user steps on foot switch 16.

High-frequency signal generation circuit 19 passes the high-frequency current having, for example, a frequency of 300 kHz to 1000 kHz and a current value of 20 mA to 200 mA (a range of current values necessary for root canal treatment to reduce an inflammation factor, bacteria, and the like in the root canal) across file 11 and passive electrode 22. It goes without saying that the high-frequency current that can be generated by high-frequency signal generation circuit 19 is not limited to having the frequency and the current value described above. The current value, frequency, energization period, and the like of the high-frequency current output from high-frequency signal generation circuit 19 can be set by operation of setting operation unit 15. Control circuit 21 controls high-frequency signal generation circuit 19 based on the current value detected by detector 20 so as to allow high-frequency signal generation circuit 19 to output the high-frequency current having the current value set via setting operation unit 15. Note that when control circuit 21 is configured not to control high-frequency signal generation circuit 19 based on the current value detected by detector 20, detector 20 need not be provided in dental treatment apparatus 10. Note that, when the energization with the high-frequency current is performed, file 11 is inserted into root canal 901, the distal end of file 11 is brought into contact with, for example, a tissue near a root apex 903, and passive electrode 22 is brought into contact with a part of a patient's body such as a gum 902 or lip 904. That is, file holder 13 is a holder that holds file 11 serving as an electrode placed at the dental treatment site, and high-frequency signal generation circuit 19 is a power supply that energizes the electrode with the high-frequency current.

Detector 20 is a current detector that detects a current value actually flowing through file 11 when the energization of file 11 with the high-frequency current is performed by high-frequency signal generation circuit 19. Control circuit 21 causes, based on the current value detected by detector 20, high-frequency signal generation circuit 19 to control the current value of the high-frequency current with which file 11 is energized. Control circuit 21 includes, as hardware components, for example, a central processing unit (CPU), a storage that stores a program, data, and the like for causing the CPU to perform the processing, a random access memory (RAM) that serves as a work area of the CPU, a graphics processing unit (GPU) that primarily performs image processing, an input/output interface for maintaining consistency of signals exchanged with peripheral devices, and the like. The storage includes a storage device such as a non-volatile memory provided inside control circuit 21, a storage device connected over a network, or the like.

Figure 4:
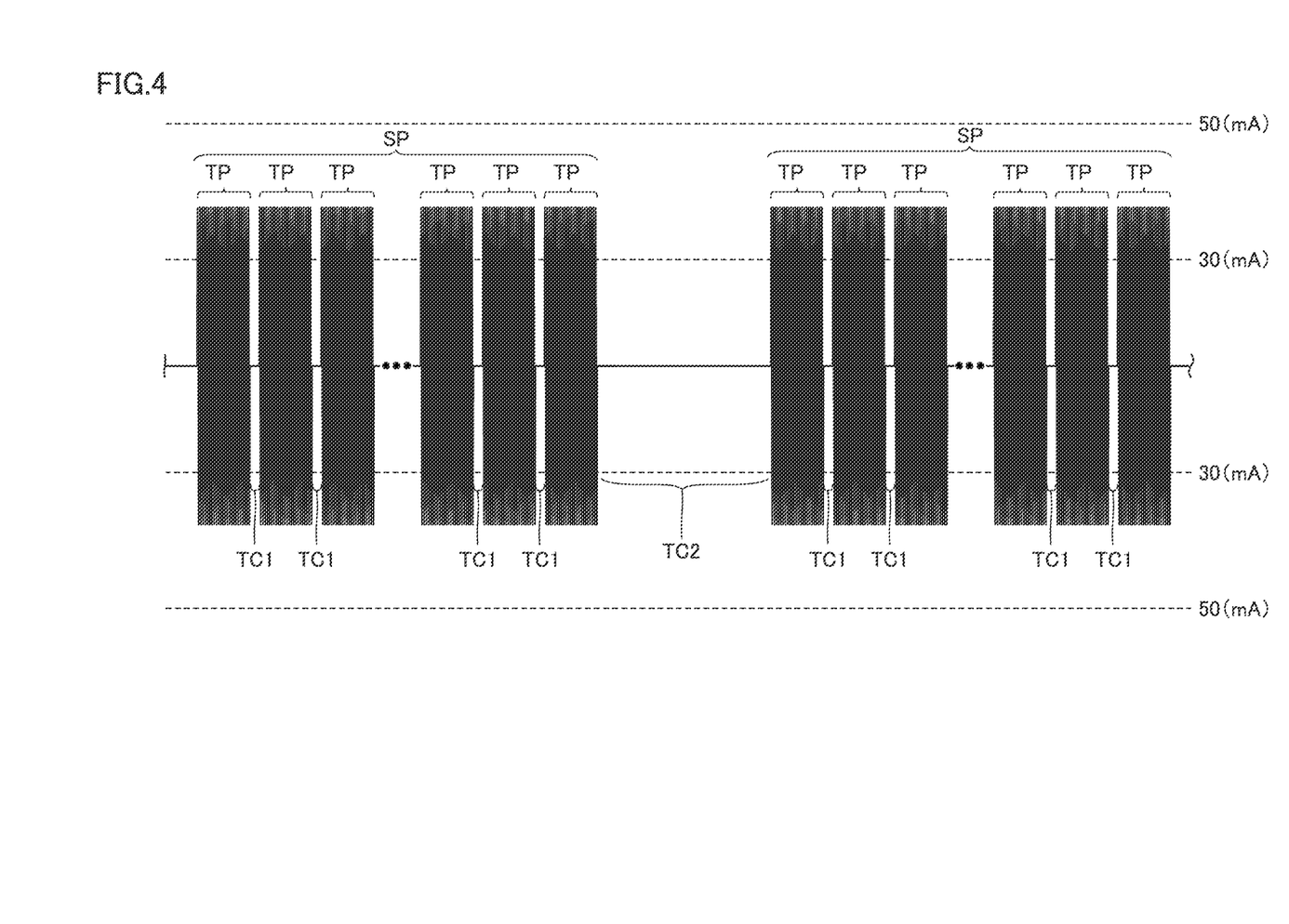
FIG. 4 is a diagram showing a waveform of a current with which the electrode of the dental treatment apparatus according to the first embodiment is energized.

Next, a description will be given of a waveform of the high-frequency current with which file 11 is energized by high-frequency signal generation circuit 19. FIG. 4 is a diagram showing a waveform of a current with which the electrode of the dental treatment apparatus according to the first embodiment is energized. Note that the diagram shown in FIG. 4 is a schematic representation, and a wavenumber shown in the diagram is different from the actual high-frequency wavenumber. The user determines the energization position of the high-frequency current and operates foot switch 16 at the energization position to cause high-frequency signal generation circuit 19 to energize file 11 with the high-frequency current. As shown in FIG. 4, high-frequency signal generation circuit 19 energizes file 11 with the high-frequency current through during a single energization period SP. Period SP is repeated while the user steps on foot switch 16. Note that period SP corresponds to the energization period.

Period SP includes a period TP where energization is continuously performed with the high-frequency current having a current value (for example, 30 mA to 50 mA) within a range of current values necessary for the root canal treatment to reduce an inflammation factor, bacteria, and the like in the root canal, and a pause period TC1 where the energization of file 11 with the high-frequency current is stopped. Specifically, high-frequency signal generation circuit 19 continuously performs energization for, for example, 0.07 seconds (70 ms) as period TP, and then continuously performs energization for, for example, 0.07 seconds (70 ms) as next period TP with a time interval of, for example, 0.03 seconds (30 ms) as pause period TC1 placed between period TP and next period TP. Usually, continuous energization period TP and pause period TC1 are each determined based on, for example, a hemostatic effect, a tissue coagulation effect, or a cauterization effect. The energization operation causes high-frequency signal generation circuit 19 to repeat continuous energization period TP and pause period TC1 (0.1 seconds (100 ms) in total) N times (for example, 10 times) during single energization period SP. In dental treatment apparatus 10, for each time the user steps on foot switch 16, high-frequency signal generation circuit 19 energizes file 11 with the high-frequency current for about 1 second (including pause period TC1). Note that the cumulative energization period of the high-frequency current is, for example, greater than or equal to 1 second.

In FIG. 4, since the user steps on foot switch 16, during the energization operation, after single energization period SP, operation corresponding to next single energization period SP is repeated with a stop period TC2 where the energization of file 11 with the high-frequency current is stopped provided between single energization period SP and next single energization period SP. Stop period TC2 is set longer than pause period TC1. For example, 0.4 seconds (400 ms) are set as stop period TC2. Dental treatment apparatus 10 can perform, during the energization operation, energization with the high-frequency current to the extent that the patient does not complain of a pain and prevent a temperature at the energized site from excessively rising by providing stop period TC2 between single energization periods SP. Here, during the energization operation, period SP corresponds to a single energization period, period TP corresponds to a continuous energization period included in period SP, pause period TC1 corresponds to a period provided between continuous energization periods TP, and stop period TC2 corresponds to a period provided between single energization periods SP.

A period where the patient feels a pain caused by the energization with the high-frequency current corresponds to period TP where energization with the high-frequency current is continuously performed, and it is preferable that period TP be shorter than stop period TC2. In FIG. 4, when period TP is set to, for example, 0.07 seconds (70 ms), it is preferable that stop period TC2 be at least twice as long as period TP, for example, 0.14 seconds (140 ms). Further, period TP where the energization with the high-frequency current is continuously performed may be shorter than or equal to 200 ms to make a period where the patient feels a pain shorter, and stop period TC2 may be longer than or equal to 400 ms. Furthermore, it is preferable that single energization period SP be shorter than stop period TC2.

Furthermore, dental treatment apparatus 10 includes root canal length measurement circuit 23. Root canal length measurement circuit 23 measures a position of the distal end of file 11 by applying a root canal length measurement signal across file 11 and passive electrode 22. Specifically, root canal length measurement circuit 23 applies voltages having two different frequencies across file 11 and passive electrode 22 to obtain respective impedance values, and determines the position of the distal end of file 11 relative to root apex 903 based on, for example, a difference or ratio between the two values (in practice, voltage or current values corresponding to the impedance values). Note that the method for measuring the root canal length is not limited to such a method, and various techniques including a measurement method proposed in the related art may be used. During the root canal length measurement, passive electrode 22 is also brought into contact with a part of the patient's body such as gum 902 or lip 904.

Switch SW1 is provided to switch the electrical connection between file 11 and high-frequency signal generation circuit 19 or root canal length measurement circuit 23. Switch SW2 is provided to switch the electrical connection between passive electrode 22 and high-frequency signal generation circuit 19 or root canal length measurement circuit 23.

Switch SW1 and switch SW2 are changes in position by control circuit 21 based on information input from setting operation unit 15. Specifically, in order to energize file 11 with the high-frequency current, control circuit 21 controls switch SW1 and switch SW2 to connect file 11 and passive electrode 22 to high-frequency signal generation circuit 19. In order to apply the root canal length measurement signal across file 11 and passive electrode 22, control circuit 21 controls switch SW1 and switch SW2 to connect file 11 and passive electrode 22 to root canal length measurement circuit 23. According to the first embodiment, switch SW1 and switch SW2 are controlled in accordance with an operation mode set via setting operation unit 15 to change connection destinations of file 11 and passive electrode 22. Further, control circuit 21 controls switch SW1 and switch SW2 to connect file 11 and passive electrode 22 to root canal length measurement circuit 23 during pause period TC1 or stop period TC2, so as to cause root canal length measurement circuit 23 to measure the position of the distal end of file 11. Note that switch SW1 and switch SW2 may be changed in position in synchronization with on/off operation of foot switch 16.

According to the first embodiment, high-frequency signal generation circuit 19 and root canal length measurement circuit 23 are electrically separated from each other by switch SW1 and switch SW2. Therefore, while high-frequency current is output to file 11, root canal length measurement circuit 23 is electrically disconnected from file 11 and passive electrode 22 by switch SW1 and switch SW2. This prevents root canal length measurement circuit 23 from being energized with the high-frequency current, so that it is possible to prevent root canal length measurement circuit 23 from failing due to the high-frequency current.

Further, according to the first embodiment, it is possible to determine where the position of the distal end of file 11 is located relative to the root apex by using root canal length measurement circuit 23. Therefore, the user can operate setting operation unit 15 to switch from a root canal length measurement mode to a high-frequency energization mode after confirming that the distal end of file 11 in the root canal has reached the position where the energization with the high-frequency current is performed by using root canal length measurement circuit 23. Dental treatment apparatus 10 can energize file 11 with the high-frequency current with the distal end of file 11 held at an appropriate position. It goes without saying that dental treatment apparatus 10 need not include root canal length measurement circuit 23 and only needs to have a capability of energizing file 11 with the high-frequency current, and may energize file 11 with the high-frequency current after confirming the position of the distal end of file 11 by using another root canal length measurement device.

Control circuit 21 may cause, based on the position of the distal end of file 11 measured by root canal length measurement circuit 23, high-frequency signal generation circuit 19 to control at least one of the current value of the high-frequency current with which file 11 is energized, continuous energization period TP, the frequency of continuous energization periods TP, or pause period TC1.

Display 14 is, for example, a liquid crystal display and serves as a notification unit that displays the current value with which file 11 is energized by high-frequency signal generation circuit 19, the position of the distal end of file 11 measured by root canal length measurement circuit 23, and the like to notify the user of dental treatment apparatus 10 of necessary information. For example, when the current value detected by detector 20 falls outside the range of current values necessary for the root canal treatment to reduce an inflammation factor, bacteria, and the like in the root canal, display 14 may output information showing that the current value of the high-frequency current with which the energization is performed falls outside the range of current values necessary for the root canal treatment. Note that display 14 may include an organic EL display, electronic paper, a light emitting diode, or the like. Further, the notification unit may be a lamp, a speaker, or the like (not shown) rather than display 14, and may output the notification to the user by turning on the lamp or by emitting a beep from a speaker.

As described above, dental treatment apparatus 10 according to the first embodiment is configured to energize the dental treatment site (for example, a root canal or the like) with the high-frequency current. Included are file holder 13 that holds file 11 placed at the dental treatment site, high-frequency signal generation circuit 19 that energizes file 11 with the high-frequency current, and control circuit 21 that causes, during the energization operation, high-frequency signal generation circuit 19 to provide stop period TC2 where the energization of file 11 with the high-frequency current is stopped between single energization period SP and next single energization period SP. Note that the cumulative energization period of the high-frequency current is preferably longer than or equal to 1 second.

With such a configuration, dental treatment apparatus 10 according to the first embodiment provides stop period TC2 between periods SP where the energization is performed in response to single energization operation, so that it is possible to perform energization with the high-frequency current to the extent that the patient does not complain of a pain and to prevent a temperature at the energized site from excessively rising.

Further, control circuit 21 may cause high-frequency signal generation circuit 19 to provide the plurality of continuous energization periods TP in single energization period SP and to interpose pause period TC1 where the energization of file 11 with the high-frequency current is paused between two adjacent periods TP. This allows dental treatment apparatus 10 to perform energization to the extent that the patient does not complain of a pain caused by continuous energization with the high-frequency current and to prevent a temperature at the energized site from excessively rising by further dividing single energization period SP into short periods TP.

Further, each of the plurality of periods TP is preferably shorter than stop period TC2. For example, each of the plurality of periods TP is preferably shorter than or equal to 200 ms, and stop period TC2 is preferably longer than or equal to 400 ms.

Dental treatment apparatus 10 may further include root canal length measurement circuit 23 that electrically measures the position of the distal end of file 11 in the root canal, and control circuit 21 may cause root canal length measurement circuit 23 to energize file 11 with a measurement signal for root canal length measurement during pause period TC1 or stop period TC2. This allows dental treatment apparatus 10 to measure the position of the distal end of file 11 even during the energization period where file 11 is energized with the high-frequency current. Furthermore, control circuit 21 may cause, based on the position of the distal end of file 11 measured by root canal length measurement circuit 23, high-frequency signal generation circuit 19 to control at least one of the current value of the high-frequency current with which file 11 is energized, continuous energization period TP, the frequency of continuous energization periods TP, or pause period TC1.

Second Embodiment

A description has been given of dental treatment apparatus 10 according to the first embodiment that energizes file 11 with the high-frequency current with periods SP made identical in length to each other and stop periods TC2 made identical in length to each other. A description will be given of a dental treatment apparatus according to a second embodiment that energizes the file with the high-frequency current with periods SP made different in length from each other and stop periods TC2 made different in length from each other. Note that, according to the second embodiment, the same components as the components of dental treatment apparatus 10 described according to the first embodiment are denoted by the same reference numerals, and no detailed description of such components will be given below.

Figure 5:
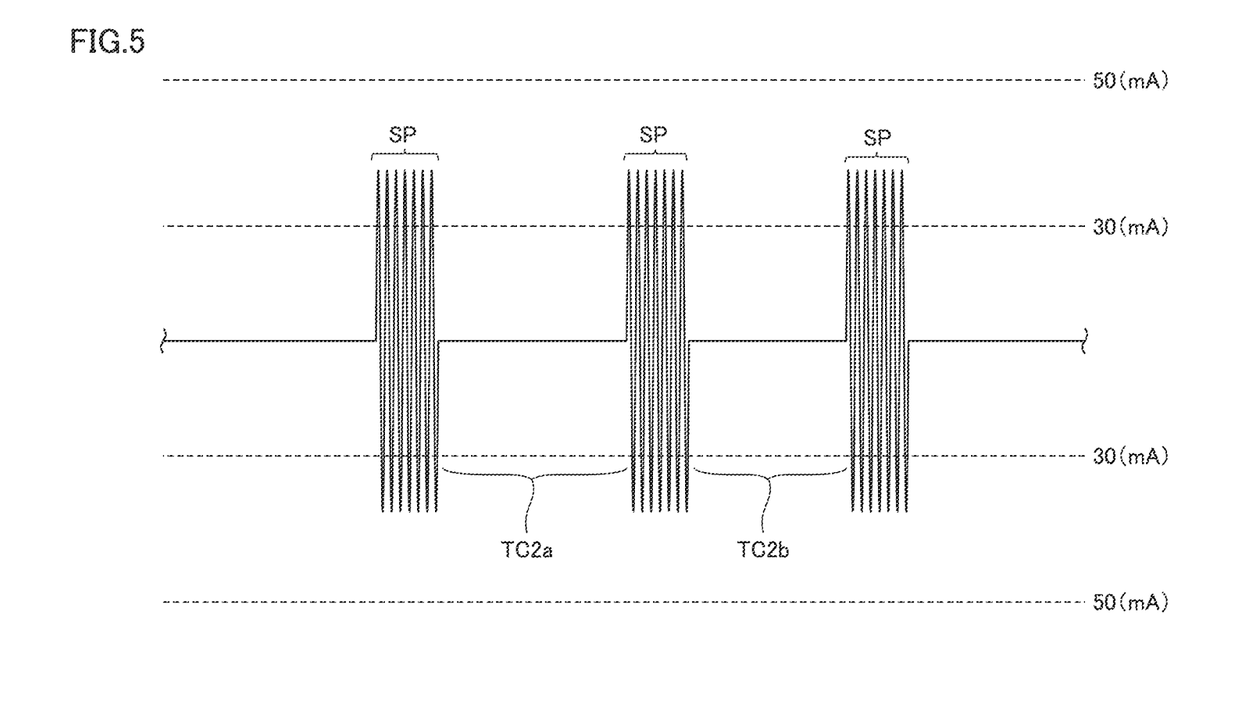
FIG. 5 is a diagram showing a waveform of a current with which an electrode of a dental treatment apparatus according to a second embodiment is energized.

First, a description will be given of a waveform of the high-frequency current with which file 11 is energized by high-frequency signal generation circuit 19 with stop periods TC2 made different in length from each other. FIG. 5 is a diagram showing a waveform of a current with which an electrode of a dental treatment apparatus according to a second embodiment is energized. Note that the diagram shown in FIG. 5 is a schematic representation, and a wavenumber shown in the diagram is different from the actual high-frequency wavenumber. Further, although FIG. 5 shows period SP without periods TP or pause periods TC1 unlike period SP shown in FIG. 4, period SP shown in FIG. 5 may include periods TP and pause periods TC1 as shown in FIG. 4.

The user determines the energization position of the high-frequency current based on root canal length measurement circuit 23, and operates foot switch 16 at the energization position to cause high-frequency signal generation circuit 19 to energize file 11 with the high-frequency current. High-frequency signal generation circuit 19 energizes file 11 with the high-frequency current during period SP shown in FIG. 5. During period SP, energization with the high-frequency current having a current value (for example, 30 mA to 50 mA) within the range of current values necessary for the root canal treatment to reduce an inflammation factor, bacteria, and the like in the root canal is performed. Note that high-frequency signal generation circuit 19 includes a constant voltage circuit and energizes file 11 with the high-frequency current to under constant voltage control. Further, high-frequency signal generation circuit 19 may be a constant current circuit, and may energize file 11 with the high-frequency current under constant current control.

Furthermore, dental treatment apparatus 10 provides a stop period TC2a where the energization of file 11 with the high-frequency current is stopped before the start of energization during next period SP so as to prevent the patient from complaining of a pain caused by the energization with the high-frequency current. In FIG. 5, the plurality of periods SP are identical in length to each other. Dental treatment apparatus 10 further provides a stop period TC2b where the energization of file 11 with the high-frequency current is stopped before the start of energization during next period SP. Stop period TC2b is set shorter than stop period TC2a. Although only three periods SP and two stop periods each provided between adjacent periods SP are shown in FIG. 5, control circuit 21 divides, when there are a plurality of stop periods, the plurality of stop periods into a first half of stop periods and a second half of stop periods and makes the first half of stop periods longer than the second half of stop periods. For example, assuming that first stop period TC2a shown in FIG. 5 belongs to the first half of stop periods, and second stop period TC2b belongs to the second half of stop periods, first stop period TC2a is set longer than second stop period TC2b. First stop period TC2a may have a length longer than or equal to, for example, 0.5 seconds that allows the patient to complain to the user about a pain.

Figure 6:
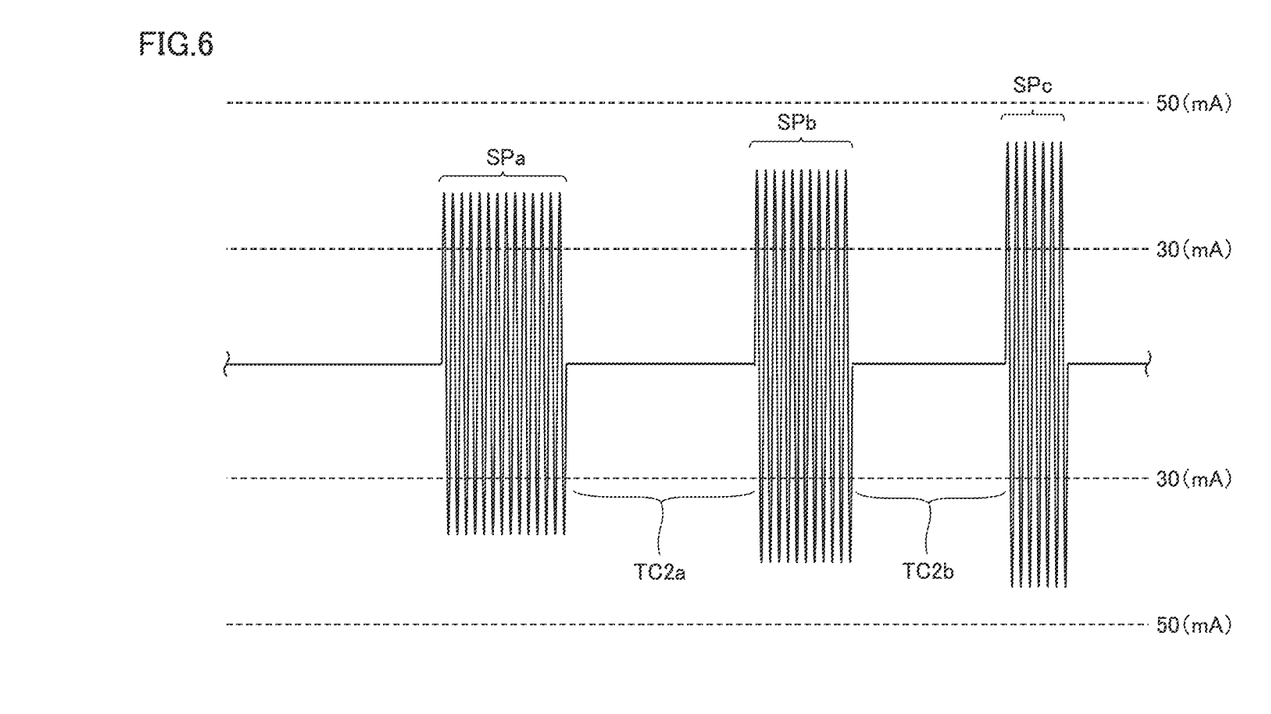
FIG. 6 is a diagram showing a waveform of a current with which an electrode of a dental treatment apparatus according to a modification of the second embodiment is energized.

Next, a description will be given of a waveform of the high-frequency current with which file 11 is energized by high-frequency signal generation circuit 19 with periods SP made different in length from each other. FIG. 6 is a diagram showing a waveform of a current with which file 11 of dental treatment apparatus 10 according to a modification of the second embodiment is energized. FIG. 6 shows a waveform of the high-frequency current with which energization is performed during periods SPa to SPc in response to single energization operation. When periods SPa to SPc are repeated in this order, control circuit 21 gradually makes a corresponding period length shorter and makes a corresponding current value larger. Note that, as shown in the waveform of FIG. 6, stop period TC2b is set shorter than stop period TC2a, but the present invention is not limited to such a configuration, and stop periods TC2 having the same length may be set. Further, although FIG. 6 shows periods SPa to SPc without periods TP or pause periods TC1 unlike period SP shown in FIG. 4, periods SPa to SPc shown in FIG. 6 may include periods TP and pause periods TC1 as shown in FIG. 4.

As shown in FIG. 6, for example, when periods SPa to SPc are repeated in this order, control circuit 21 gradually makes a corresponding period length shorter so as to energize file 11 with the high-frequency current with second period SPb made shorter than first period SPa, and third period SPc made shorter than second period SPb. Further, when periods SPa to SPc are repeated in this order, control circuit 21 may gradually make a corresponding current value larger so as to energize file 11 with the high-frequency current with the current value for second period SPb made larger than the current value for first period SPa, and the current value for third period SPc made larger than the current value for second period SPb. Further, control circuit 21 energizes file 11 with the high-frequency current with first stop period TC2a made longer than second stop period TC2b among the plurality of stop periods. When the stop period is made longer, it is possible to perform energization with the high-frequency current to the extent that the patient feels no pain and to prevent heat generated by the energization with the high-frequency current from being stored. Note that, when the stop time is made longer as shown in the waveform of FIG. 6, the entire treatment period becomes longer accordingly.

As described above, in dental treatment apparatus 10 according to the second embodiment, when control circuit 21 divides the plurality of stop periods into the first half of stop periods TC2a and the second half of stop periods TC2b, the first half of stop periods TC2a is preferably made longer than the second half of stop periods TC2b. This allows dental treatment apparatus 10 to perform energization with the high-frequency current to the extent that the patient feels no pain and to prevent heat generated by the energization with the high-frequency current from being stored. Further, when the plurality of periods SPa to SPc are repeated in this order, control circuit 21 may gradually make a corresponding period length shorter. Furthermore, when the plurality of periods SPa to SPc are repeated in this order, control circuit 21 may gradually make a corresponding current value larger.

Third Embodiment

A description has been given of dental treatment apparatus 10 according to the first embodiment that energizes file 11 with the high-frequency current having the current value set in advance by setting operation unit 15. As for a third embodiment, a description will be given in detail of how to control the current value of the high-frequency current with which file 11 is energized. Note that, according to the third embodiment, the same components as the components of dental treatment apparatus 10 described according to the first embodiment are denoted by the same reference numerals, and no detailed description of such components will be given below.

An electrode inserted into a root canal may have an insulating film formed on a surface of the electrode due to energization with a current. In particular, when sparks are produced from the electrode during the energization with the high-frequency current, it is highly likely that the surface of the electrode is denatured, and this denaturation of the surface of the electrode not only changes the conductivity of the electrode, but also forms an insulating film on the surface of the electrode. When the insulating film is formed on the surface of the electrode, a resistance value of the electrode increases, a current value flowing through the electrode decreases, and a current value necessary for the root canal treatment to reduce an inflammation factor, bacteria, and the like in the root canal cannot be obtained, so that an expected treatment effect may not be obtained. Here, the current value necessary for the root canal treatment to reduce an inflammation factor, bacteria, and the like in the root canal is a current value within a range of current values at which the expected treatment effect can be obtained by energizing, with the high-frequency current, the electrode placed at the dental treatment site, and there is a possibility that a sufficient treatment effect cannot be obtained with a current value smaller than the range, and conversely, periodontal tissue and the like are damaged with a current value larger than the range.

Furthermore, blood, protein, or the like may adhere to and coagulate on the electrode inserted into the root canal. When blood, protein, or the like adheres to and coagulates on the electrode, the resistance value of the electrode increases, the current value flowing through the electrode decreases, and the current value necessary for the root canal treatment cannot be obtained, so that the expected treatment effect cannot be obtained. Further, the root canal varies in impedance in a manner that depends on the state of the root canal into which the electrode is inserted, so that a current value greater than the current value necessary for the root canal treatment may flow, or only a current value less than the current value necessary for the root canal treatment may flow. For example, when an apical foramen is large, the root canal is filled with a conductive medical fluid, or foreign matter in the root canal burns off due to the high-frequency current, the impedance of the root canal decreases, so that a current having a current value greater than the current value necessary for the root canal treatment flows. Further, in general, the more the periodontal tissue dries, the larger the impedance, so that only a current value less than the current value necessary for the root canal treatment can flow.

Figure 7:
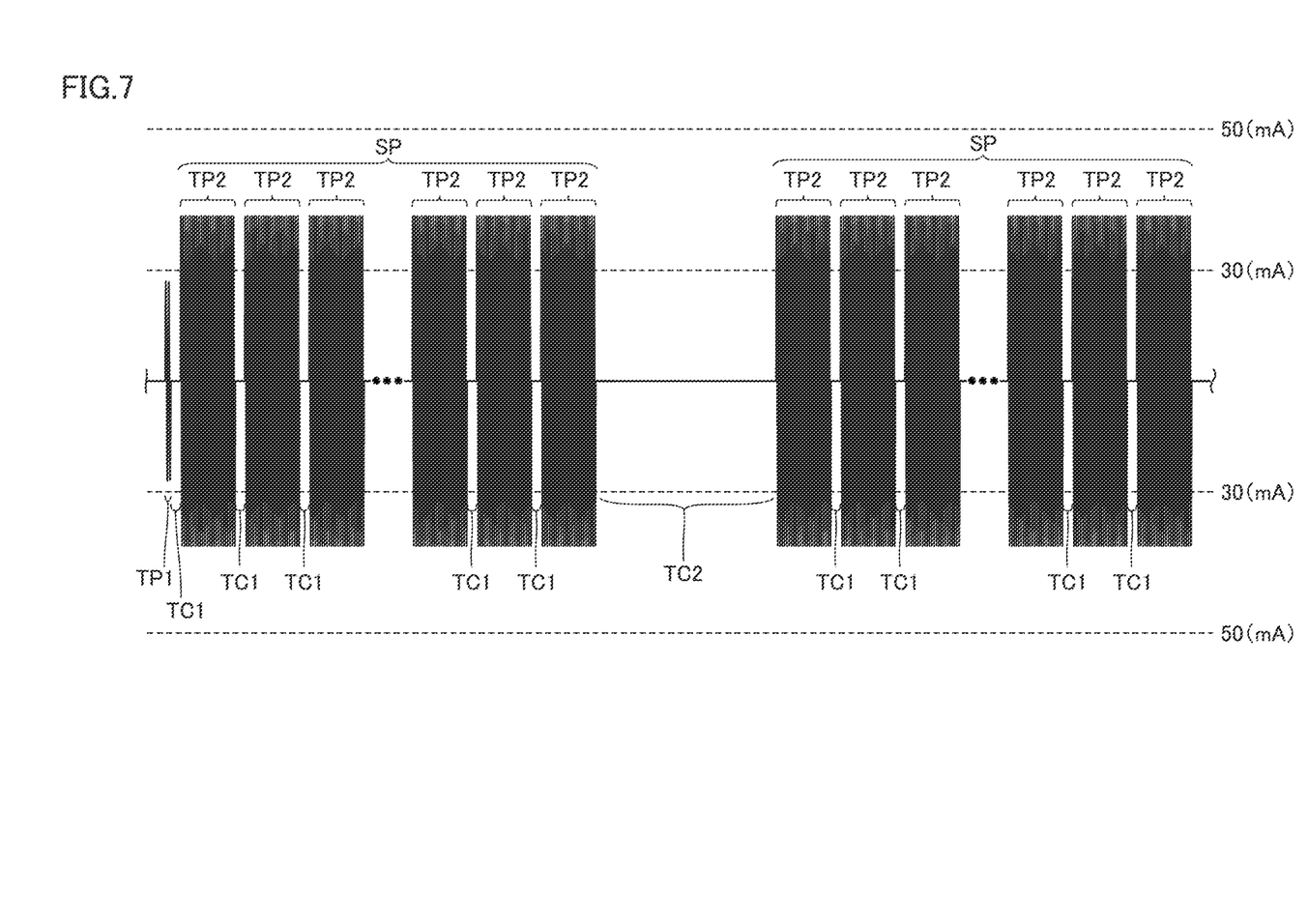
FIG. 7 is a diagram showing a waveform of a current with which an electrode of a dental treatment apparatus according to a third embodiment is energized.

Therefore, dental treatment apparatus 10 according to the third embodiment performs control so as to allow energization with a smaller current value as a preliminary current to be performed before full energization and allow, based on the current value, energization with the high-frequency current having a current value necessary for the root canal treatment to reduce an inflammation factor, bacteria, and the like in the root canal to be performed during the full energization. FIG. 7 is a diagram showing a waveform of a current with which an electrode of a dental treatment apparatus according to a third embodiment is energized. FIG. 7 shows a waveform where period SP that is the full energization period is repeated a plurality of times after period TP1 where the preliminary energization is performed.

As shown in FIG. 7, dental treatment apparatus 10 determines, based on the current value of the preliminary current detected during period TP1, the current value of the high-frequency current with which file 11 is energized during continuous energization period TP2 in period SP. FIG. 7 shows a waveform of next period SP after period SP that is the full energization period is provided after period TP1 where the preliminary energization is performed. Control circuit 21 controls period SP so as to make the plurality of periods TP2 identical in length to each other and make each of the plurality of periods TP2 longer than pause period TC1. Further, control circuit 21 performs control so as to provide stop period TC2 where the energization of file 11 with the high-frequency current is stopped between period SP and next period SP. Note that stop period TC2 is made longer than pause period TC1.

When it is assumed that a path extending from file 11 to passive electrode 22 has a normal impedance, control circuit 21 controls the voltage of high-frequency signal generation circuit 19 so as to energize file 11 with the current value of the preliminary current. Then, when a preliminary voltage is applied to cause high-frequency signal generation circuit 19 to energize file 11 with the preliminary current, and the impedance of the path extending from file 11 to passive electrode 22 changes from the normal impedance, the current value detected by detector 20 becomes different from an expected current value of the preliminary current. The impedance of the path extending from file 11 to passive electrode 22 varies in a manner that depends on the presence or absence of the insulating film formed on the surface of file 11, the presence or absence of adhesion of blood, protein, and the like to the surface of file 11, the impedance of the root canal, or the like.

Control circuit 21 performs control based on the current value detected by detector 20 when the preliminary current flows through file 11 so as to bring the current value of the high-frequency current flowing from high-frequency signal generation circuit 19 to file 11 for the energization during period TP2 within a predetermined range. That is, in accordance with a difference or a ratio between a predicted current value of the preliminary current and the current value detected by detector 20, control circuit 21 changes an optimum voltage at which the current value of the high-frequency current flowing through file 11 falls within the predetermined range and applies the optimum voltage thus changed to high-frequency signal generation circuit 19. That is, control circuit 21 optimizes the voltage applied to high-frequency signal generation circuit 19 so as to bring the current value of the high-frequency current flowing through file 11 within the predetermined range. Here, the predetermined range is a range of current values necessary for the root canal treatment to reduce an inflammation factor, bacteria, and the like in the root canal, and there are three possible ranges as the predetermined range according to symptoms: (1) greater than or equal to the predetermined value, (2) less than or equal to the predetermined value, and (3) greater than or equal to a first predetermined value and less than or equal to a second predetermined value (>the first predetermined value). In general, (3) greater than or equal to the first predetermined value and less than or equal to the second predetermined value (>the first predetermined value) is often used. Note that the current value of the high-frequency current flowing through file 11 is not limited to the current value necessary for the root canal treatment to reduce an inflammation factor, bacteria, and the like in the root canal. Further, although a description has been given of the configuration where control circuit 21 makes a comparison based on a difference between the current value of the preliminary current and the current value detected by detector 20, another comparison method using, for example, a ratio may be employed.

As described above, control circuit 21 performs feedback control on the current value with which energization is performed during period TP2 based on a result of detecting the preliminary current. When the current value of the high-frequency current is feedback-controlled during period SP, and the current value detected by detector 20 changes and falls outside the predetermined range, control circuit 21 may display information showing that the current value falls outside the predetermined range on display 14. For example, when foreign matter in the root canal comes off and the current value detected by detector 20 changes to 60 mA, 90 mA, and 80 mA, display 14 outputs a warning display showing that the current value falls outside the predetermined range. Note that when the current value detected by detector 20 falls within the predetermined range but changes by at least a predetermined percentage (for example, about ±30%), information showing that the current value of the high-frequency current with which energization is performed changes abruptly may be displayed on display 14. It goes without saying that, when the current value falls outside the predetermined range, control circuit 21 may control the voltage to be applied to high-frequency signal generation circuit 19 so as to bring the current value of the high-frequency current with which file 11 is energized within the predetermined range.

Figure 8:
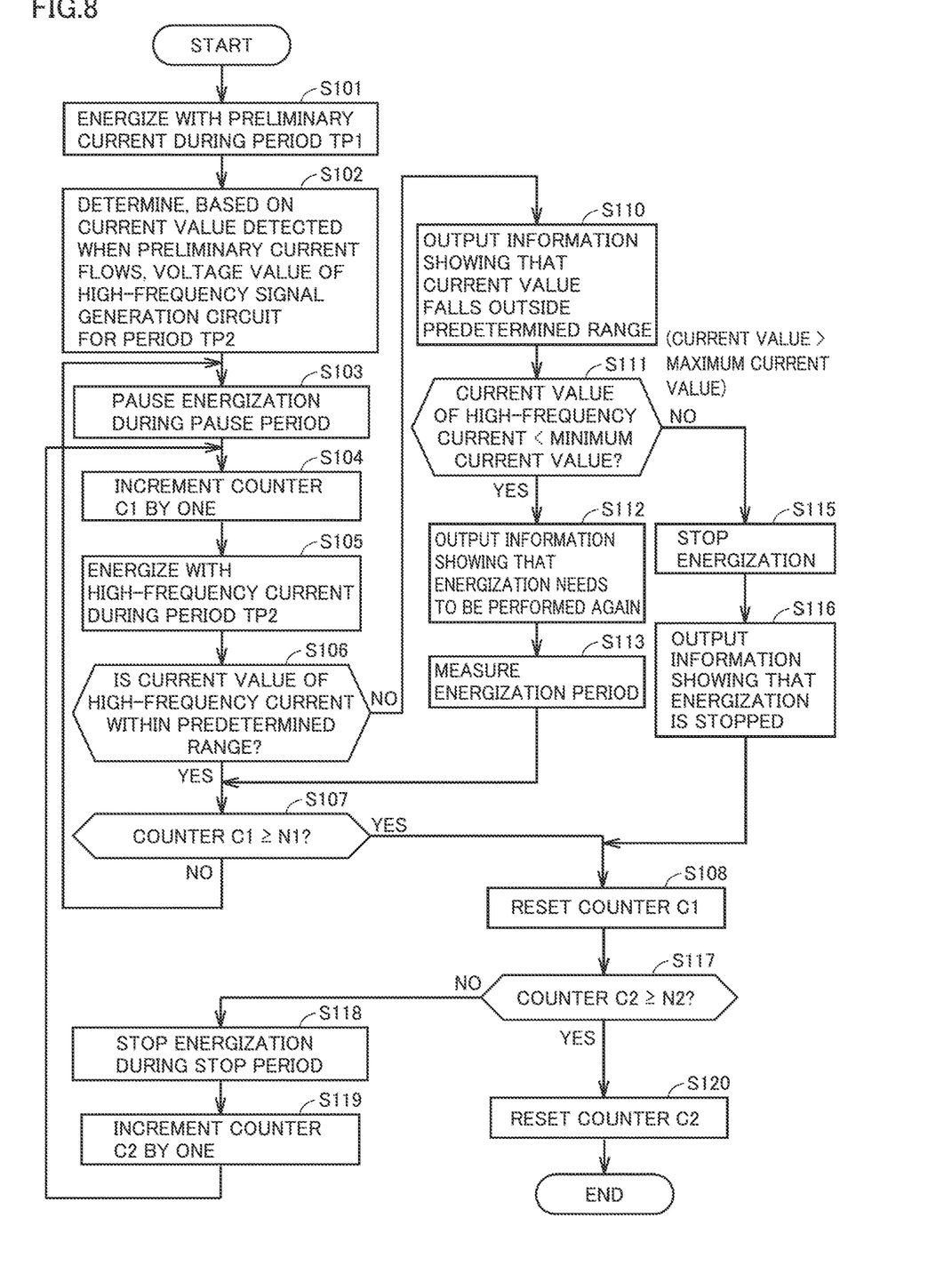
FIG. 8 is a flowchart for describing control of the dental treatment apparatus according to the third embodiment.

Next, a description will be given with reference to a flowchart of how to control the energization period of the high-frequency current with which file 11 is energized in dental treatment apparatus 10 according to the third embodiment. FIG. 8 is a flowchart for describing control of the dental treatment apparatus according to the third embodiment. First, when the user determines the energization position of the high-frequency current based on root canal length measurement circuit 23 and operates foot switch 16 at the energization position, control circuit 21 causes high-frequency signal generation circuit 19 to energize file 11 with the preliminary current during period TP1 (step S101).

Next, control circuit 21 determines, based on the current value detected by detector 20 when the preliminary current flows through file 11, the voltage value of high-frequency signal generation circuit 19 for energizing file 11 with the current value of the high-frequency current that falls within the range (hereinafter, also referred to as a predetermined range) of current values necessary for the root canal treatment to reduce an inflammation factor, bacteria, and the like in the root canal (step S102). Specifically, control circuit 21 calculates the impedance of the root canal from the current value detected by detector 20 and a corresponding voltage value applied to high-frequency signal generation circuit 19, and determines the voltage value of high-frequency signal generation circuit 19 that brings the current value with which file 11 is energized with the root canal having the impedance within the predetermined range.

After the elapse of period TP1 where the preliminary energization is performed, control circuit 21 pauses the energization of file 11 by high-frequency signal generation circuit 19 during pause period TC1 (step S103). Note that control circuit 21 may switch from the high-frequency energization mode to the root canal length measurement mode to measure the position of the distal end of file 11 during pause period TC1. That is, control circuit 21 may cause root canal length measurement circuit 23 to energize file 11 with the measurement signal during pause period TC1.

In order to count the frequency of energization with the high-frequency current during period TP2, control circuit 21 increments an energization frequency counter C1 by one (step S104). Control circuit 21 applies the voltage value determined in step S102 to high-frequency signal generation circuit 19 to cause high-frequency signal generation circuit 19 to energize file 11 with the current value within the predetermined range during period TP2 (step S105). Control circuit 21 determines whether the current value detected by detector 20 when the voltage value determined in step S102 is applied to high-frequency signal generation circuit 19 falls within the predetermined range (step S106).

When the detected current value falls within the predetermined range (YES in step S106), control circuit 21 determines whether energization frequency counter C1 is greater than or equal to N1 (for example, 10) (step S107). When energization frequency counter C1 is not greater than or equal to N1 (NO in step S107), control circuit 21 returns the processing to step S101 and repeats the control of pause period TC1 and period TP2. When returning the processing to step S101, control circuit 21 provides pause period TC1 (not shown). Alternatively, when energization frequency counter C1 is not greater than or equal to N1 (NO in step S107), control circuit 21 may return the processing to step S103 and repeats the control of pause period TC1 and period TP2. On the other hand, when energization frequency counter C1 is greater than or equal to N1 (YES in step S107), control circuit 21 resets energization frequency counter C1 to 0 (zero) (step S108).

Returning to step S106, when the detected current value falls outside the predetermined range (NO in step S106), control circuit 21 displays, on display 14, information showing that the current value of the high-frequency current with which energization is performed falls outside the predetermined range (step S110). Specifically, when foreign matter in the root canal comes off during the energization of file 11 with the high-frequency current, and the current value detected by detector 20 falls outside the predetermined range (30 mA to 50 mA) and changes to 60 mA, 90 mA, and 80 mA, control circuit 21 may display a string "falls outside the predetermined range" on display 14 or change the background color of the screen to yellow. When a speaker is provided as the notification unit, the user may be notified, by a warning beep, of information showing that the current value of the high-frequency current with which energization is performed falls outside the predetermined range.

Next, even when the voltage value determined in step S102 is applied to high-frequency signal generation circuit 19, control circuit 21 determines whether the current value detected by detector 20 is less than the minimum current value of the predetermined range (step S111). When the detected current value falls outside the predetermined range (NO in step S105) and is less than the minimum current value of the predetermined range (YES in step S111), control circuit 21 displays, on display 14, information showing that the process of energizing file 11 with the high-frequency current needs to be performed again (step S112). Specifically, control circuit 21 possibly displays a string "re-energization" on display 14, or causes the screen to blink with the background color set to yellow. When a speaker is provided as the notification unit, the user may be notified, by a warning beep, of information showing that energization needs to be performed again.

Further, control circuit 21 measures the energization period where the detected current value is less than the minimum current value of the predetermined range (step S113). In the flowchart shown in FIG. 8, the process of energizing file 11 with the high-frequency current is stopped when the control of pause period TC1 and period TP2 has been repeated N1 times rather than when the detected current value becomes less than the minimum current value of the predetermined range. Therefore, control circuit 21 can measure period TP2 where the detected current value is less than the minimum current value of the predetermined range based on how many times period TP2 where the detected current value is less than the minimum current value has appeared among the repetitions N1. In order to perform energization again, control circuit 21 may perform, by measuring period TP2 where the detected current value is less than the minimum current value, the energization only during the period measured in step S113. It goes without saying that, when the process of energizing file 11 with the high-frequency current is stopped when the detected current value becomes less than the minimum current value of the predetermined range, control circuit 21 may execute step S108 after step S113. Here, the case where the detected current value can be determined to be less than the minimum current value of the predetermined range corresponds to a case where the environment in the root canal changes during energization, the impedance of the root canal increases, and a current value less than the minimum current value of the predetermined range flows accordingly. Further, when the detected current value is less than the minimum current value of the predetermined range, control circuit 21 may perform control so as to increase the voltage applied to high-frequency signal generation circuit 19 to make the current value of the high-frequency current with which file 11 is energized greater than or equal to the minimum current value of the predetermined range.

Returning to step S111, when the detected current value falls outside the predetermined range (NO in step S105) and is not less than the minimum current value of the predetermined range (NO in step S111), control circuit 21 can determine that the detected current value is greater than the maximum current value of the predetermined range, and thus stops the process of energizing file 11 with the high-frequency current (step S115). Note that control circuit 21 stops the energization when the current value detected after the start of the full energization becomes greater than the maximum current value of the predetermined range as in step S115, but does not start the full energization at all when the current value detected during the preliminary energization becomes greater than the maximum current value of the predetermined range. Control circuit 21 displays, on display 14, information showing that the process of energizing file 11 with the high-frequency current is stopped (step S116). Specifically, control circuit 21 possibly displays a string "stop" on display 14 or causes the screen to blink with the background color set to red. When a speaker is provided as the notification unit, the user may be notified, by a warning beep, of information showing that energization is stopped. Here, the case where the detected current value can be determined to be greater than the maximum current value of the predetermined range corresponds to a case where the environment in the root canal changes during energization, the impedance of the root canal decreases, and a current value greater than the minimum current value of the predetermined range flows accordingly.

Further, when the detected current value is greater than the maximum current value of the predetermined range, control circuit 21 may perform control so as to decrease the voltage applied to high-frequency signal generation circuit 19 to make the current value of the high-frequency current with which file 11 is energized less than or equal to the maximum current value of the predetermined range.

Dental treatment apparatus 10 according to the third embodiment repeats, N2 times (for example, 5 times), period SP where pause period TC1 and period TP2 are repeated N1 times to energize file 11 with high-frequency current. Therefore, after resetting energization frequency counter C1 in step S108, control circuit 21 determines whether a period frequency counter C2 used for counting the frequency of periods SP is greater than or equal to N2 (step S117). When period frequency counter C2 is not greater than or equal to N2 (NO in step S117), control circuit 21 stops the energization of file 11 by high-frequency signal generation circuit 19 during stop period TC2 (step S118). In order to count the frequency of energization periods where energization with the high-frequency current is performed, control circuit 21 increments period frequency counter C2 by one (step S119).

After counting period frequency counter C2 in step S119, control circuit 21 returns the processing to step S104 and repeats the control of pause period TC1 and period TP2. On the other hand, when period frequency counter C2 is greater than or equal to N2 (YES in step S117), control circuit 21 resets period frequency counter C2 to 0 (zero) (step S120) and stops the process of energizing file 11 with the high-frequency current.

As described above, in dental treatment apparatus 10 according to the third embodiment, control circuit 21 causes, based on the current value detected by detector 20, high-frequency signal generation circuit 19 to control at least one of the current value of the high-frequency current with which file 11 is energized, continuous energization period TP2, the frequency of continuous energization periods TP2, or pause period TC1. This allows dental treatment apparatus 10 to energize file 11 placed at the dental treatment site with the high-frequency current having a current value within the predetermined range even under various changing situations.

(Modification)

In dental treatment apparatus 10 according to the above-described embodiments, detector 20 that detects the current value with which file 11 is energized by high-frequency signal generation circuit 19 may be provided, and control circuit 21 may cause high-frequency signal generation circuit 19 to control at least one of the current value of the high-frequency current with which file 11 is energized, period TP2 where file 11 is continuously energized with the high-frequency current, the frequency (number) of periods TP2 where file 11 is continuously energized with the high-frequency current, or pause period TC1 so as to make the product of the current value detected by detector 20 and the plurality of periods TP2 where energization with the high-frequency current is continuously performed greater than or equal to a predetermined value.

Furthermore, in dental treatment apparatus 10 according to the above-described embodiments, the frequency of the high-frequency current is preferably set higher than or equal to 300 kHz in order to ensure that a person feels as less pain as possible during the energization with the high-frequency current.

Further, a description has been given of dental treatment apparatus 10 according to the above-described embodiments that divides period SP where file 11 is energized by high-frequency signal generation circuit 19 into a plurality of periods, but the period where granulation is cauterized may be divided from period SP. If only the granulation surface can be cauterized, subsequent granulation cauterization does not cause much pain, thereby allowing dental treatment apparatus 10 to divide only a period where the granulation surface can be cauterized from period SP. For example, period SP may be divided such that energization for 0.2 seconds, pause for 0.8 seconds, energization for 0.2 seconds, and pause for 0.8 seconds are sequentially performed, and then continuous energization for 0.6 seconds is performed.

The dental treatment apparatus is not limited to a configuration where file holder 13 to which file 11 is attached is provided to allow the measurement of the root canal length and the energization with the high-frequency current to be made as described in the above embodiments, and may be combined with a configuration where the treatment tool is motor-driven, a configuration where the treatment tool is ultrasonic-driven, or the like.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A dental treatment apparatus that energizes a dental treatment site with a high-frequency current, the dental treatment apparatus comprising:
   a holder configured to hold an electrode placed at the dental treatment site;
   a power supply configured to energize the electrode with the high-frequency current; and
   controller circuitry configured to:
      cause, during energization operation, the power supply to provide a stop period where energization of the electrode with the high-frequency current is stopped between a single energization period and a next single energization period, and
      cause the power supply to provide a plurality of continuous energization periods in the single energization period and to interpose a pause period where the energization of the electrode with the high-frequency current is paused between two adjacent continuous energization periods,
   wherein the pause period is shorter than the continuous energization period, and the stop period is more than twice the continuous energization period.

2. The dental treatment apparatus according to claim 1, wherein
   each of the plurality of continuous energization periods is shorter than or equal to 200 ms, and the stop period is longer than or equal to 400 ms.

3. The dental treatment apparatus according to claim 1, wherein
   when dividing a plurality of stop periods into a first half of the stop periods and a second half of the stop periods, the controller circuitry is further configured to make the first half of the stop periods longer than the second half of the stop periods.

4. The dental treatment apparatus according to claim 2, wherein
   when dividing a plurality of stop periods into a first half of the stop periods and a second half of the stop periods, the controller circuitry is further configured to make the first half of the stop periods longer than the second half of the stop periods.

5. The dental treatment apparatus according to claim 1, wherein
   each time the single energization period is repeated, the controller circuitry is further configured to make a corresponding period length shorter.

6. The dental treatment apparatus according to claim 2, wherein
   each time the single energization period is repeated, the controller circuitry is further configured to make a corresponding period length shorter.

7. The dental treatment apparatus according to claim 3, wherein
   each time the single energization period is repeated, the controller circuitry is further configured to make a corresponding period length shorter.

8. The dental treatment apparatus according to claim 1, wherein each time the single energization period is repeated, the controller circuitry is further configured to make a corresponding current value larger.

9. The dental treatment apparatus according to claim 1, wherein the dental treatment site is a root canal,
   wherein the dental treatment apparatus further comprises root canal length measurement circuitry configured to electrically measure a position of a distal end of the electrode in the root canal,
   wherein the controller circuitry is further configured to cause the root canal length measurement circuitry to energize the electrode with a measurement signal for root canal length measurement during the pause period or the stop period.

10. The dental treatment apparatus according to claim 9, wherein
    the controller circuitry is further configured to cause, based on the position of the distal end of the electrode measured by the root canal length measurement circuitry, the power supply to control at least one of: a current value of the high-frequency current which energizes the electrode, an energization period, frequencies of the energization periods, or the pause period.

11. The dental treatment apparatus according to claim 1, further comprising:
    a detector configured to detect a current value which energizes the electrode, wherein
    the controller circuitry is further configured to cause, based on the current value detected by the detector, the power supply to control at least one of: a current value of the high-frequency current which energizes the electrode, a continuous energization period, frequencies of the plurality of continuous energization periods, or the pause period.

12. The dental treatment apparatus according to claim 1, further comprising:
    a detector configured to detect a current value which energizes the electrode, wherein
    the controller circuitry is further configured to cause the power supply to control at least one of: a current value of the high-frequency current which energizes the electrode, a continuous energization period, a frequency of the plurality of continuous energization periods, or the pause period to make a product of the current value, detected by the detector, and a plurality of energization periods, in which the energization with the high-frequency current is performed, greater than or equal to a predetermined value.

13. The dental treatment apparatus according to claim 1, wherein
    the high-frequency current has a frequency higher than or equal to 300 KHz.

14. The dental treatment apparatus according to claim 1, wherein
    a cumulative energization period of the high-frequency current is longer than or equal to 1 second.

* * * * *